(12) United States Patent
Tokumaru

(10) Patent No.: US 9,448,249 B2
(45) Date of Patent: Sep. 20, 2016

(54) DISPENSING APPARATUS

(71) Applicant: Panasonic Healthcare Holdings Co., Ltd., Minato-ku, Tokyo (JP)

(72) Inventor: Tomoyoshi Tokumaru, Gunma-ken (JP)

(73) Assignee: PANASONIC HEALTHCARE HOLDINGS CO., LTD., Minato-Ku, Tokyo (JP)

( * ) Notice: Subject to any disclaimer, the term of this patent is extended or adjusted under 35 U.S.C. 154(b) by 108 days.

(21) Appl. No.: 14/279,516

(22) Filed: May 16, 2014

(65) Prior Publication Data

US 2015/0369834 A1 Dec. 24, 2015

Related U.S. Application Data

(63) Continuation of application No. 13/548,427, filed on Jul. 13, 2012, now Pat. No. 8,765,079.

(30) Foreign Application Priority Data

Jul. 14, 2011 (JP) .................. 2011-155925

(51) Int. Cl.
*B01L 3/02* (2006.01)
*G01N 35/10* (2006.01)
*C12M 1/22* (2006.01)
*C12M 3/00* (2006.01)
*C12M 1/00* (2006.01)
*C12M 1/26* (2006.01)
*C12M 1/36* (2006.01)
*B01L 9/00* (2006.01)

(52) U.S. Cl.
CPC ........... *G01N 35/1011* (2013.01); *B01L 3/021* (2013.01); *B01L 9/52* (2013.01); *B01L 9/54* (2013.01); *C12M 23/10* (2013.01); *C12M 23/48* (2013.01); *C12M 29/00* (2013.01); *C12M 33/04* (2013.01); *C12M 41/48* (2013.01); *B01L 2200/025* (2013.01); *B01L 2400/0487* (2013.01)

(58) Field of Classification Search
CPC ........ C12M 1/22; C12M 1/26; C12M 1/264; C12M 1/268; B01L 3/0227
USPC ........................................ 422/509
See application file for complete search history.

(56) References Cited

U.S. PATENT DOCUMENTS

| | | | |
|---|---|---|---|
| 3,077,780 A | 2/1963 | Takatsy | |
| 4,347,750 A | 9/1982 | Tersteeg et al. | |
| 5,629,201 A * | 5/1997 | Nugteren | C12M 23/10 422/504 |
| 5,906,795 A * | 5/1999 | Nakashima | B01L 3/0275 422/509 |
| 5,927,351 A * | 7/1999 | Zhu | A61M 5/1785 141/329 |

(Continued)

FOREIGN PATENT DOCUMENTS

JP 2009-291103 A 12/2009

*Primary Examiner* — Jyoti Nagpaul
*Assistant Examiner* — Brittany Fisher
(74) *Attorney, Agent, or Firm* — Cantor Colburn LLP

(57) ABSTRACT

A dispensing apparatus includes: a dish mounting portion having a mounting surface configured to be mounted with a dish having a bottom surface and a side surface surrounding the bottom surface; a syringe, arranged above the dish mounting portion, having a nozzle configured to discharge liquid toward an interior of the dish; and a first driving portion configured to rotate an inner bottom surface of the dish mounted on the dish mounting portion with respect to a first axis as a center of rotation, wherein the first axis is parallel to the mounting surface of the dish mounting portion.

9 Claims, 11 Drawing Sheets

(56) References Cited

U.S. PATENT DOCUMENTS

| | | | |
|---|---|---|---|
| 7,374,720 B2* | 5/2008 | Toi | G01N 35/1011 222/267 |
| 7,748,417 B2* | 7/2010 | Arcuri | B67D 1/0894 141/192 |
| 2004/0018119 A1* | 1/2004 | Massaro | B01L 3/022 422/509 |
| 2004/0096365 A1 | 5/2004 | Toi et al. | |
| 2008/0060719 A1* | 3/2008 | Massaro | G01N 35/0099 141/237 |
| 2009/0007703 A1* | 1/2009 | Angus | B01L 3/0279 73/864.14 |

* cited by examiner

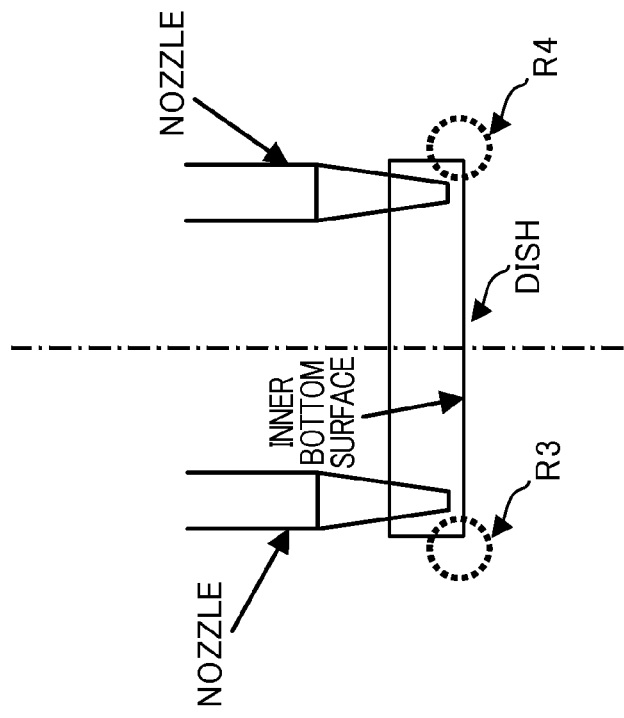
FIG. 11A —PRIOR ART—
WHEN DRIVEN FORWARD/BACKWARD AND UPWARD/DOWNWARD FROM THE CENTER OF DISH <SIDE VIEW>
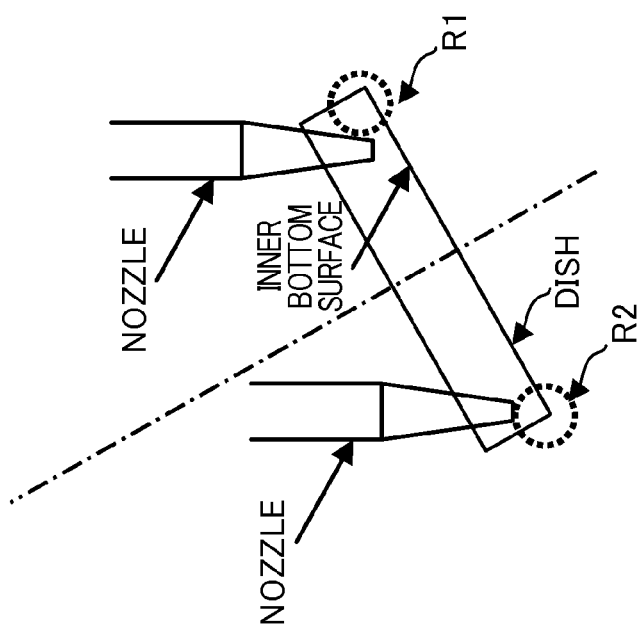
FIG. 11B —PRIOR ART—
WHEN DRIVEN LEFTWARD AND RIGHTWARD FROM THE CENTER OF DISH <FRONT VIEW>

DISPENSING APPARATUS

CROSS-REFERENCE TO RELATED APPLICATION

This is a continuation of application Ser. No. 13/548,427 filed on Jul. 13, 2012, which claims the benefit of priority to Japanese Patent Application No. 2011-155925, filed Jul. 14, 2011, of which full contents are incorporated herein by reference.

BACKGROUND OF THE INVENTION

1. Field of the Invention

The present invention relates to a dispensing apparatus.

2. Description of the Related Art

A dispensing apparatus configured to discharge liquid from a nozzle using a syringe, etc., has been used for various purposes.

For example, Japanese Patent Application Laid-open Publication No. 2009-291103 discloses an automatic cell culture apparatus including a dispensing apparatus (pipette device) to be used in a pipetting operation applied to a dish (or culture container).

Here, for example, when a cell is cultivated in a dish or a cell is passaged, operations are performed such as an operation of replacing a medium in a dish with a new medium, an operation of recovering a medium from a dish after cell cultivation is finished, an operation of recovering cell, an operation of isolating cells and an operation of adjusting a colony to a predetermined size. When these operations are performed, such considerations are required that an old culture media, reagent, and cell suspension are efficiently recovered as well as a new medium and reagent are promptly spread over an entire cell culture surface.

However, for instance, as illustrated in FIG. 11, in related dispensing apparatuses, peripheral portions in an inner bottom surface of a dish include areas on which liquid discharged from a nozzle of a syringe is unable to be poured directly. Therefore, there is such a problem that cells remains in areas on which discharged liquid cannot be poured directly. There is also another problem that cells such as a lightly attached cell, which is nearly detached by detachment solution such as trypsin, and a cell, which is deposited on and adhered to a bottom surface of a dish, cannot be recovered without directly pouring liquid to the cells for a predetermined period of time with a predetermined flow rate.

When liquid is discharged from a nozzle by tilting a dish as illustrated in FIG. 11A, since the nozzle of a syringe is directed in a vertical direction and the nozzle therefore interferes with a side surface of the tilted dish, liquid discharged from the nozzle cannot be directly poured to an area in the vicinity of the uppermost part (area illustrated as R1) out of an area of circumference of an inner bottom surface of a dish. Further, since liquid discharged from the nozzle is promptly accumulated in an area in the vicinity of the lowermost part (area illustrated as R2) out of an area of circumference of an inner bottom surface of a dish, it is also impossible to directly pour liquid discharged from a nozzle onto the area.

Furthermore, when liquid is discharged from a nozzle by tilting a dish as illustrated in FIG. 11B, since the nozzle of a syringe is directed in a vertical direction and the nozzle therefore interferes with a side surface of the dish, as in the case of the area R1, it is impossible to directly pour liquid discharged from a nozzle to areas in the vicinity of the areas intermediate between the uppermost part and the lowermost part (areas illustrated as R3 and R4) out of an area of circumference of an inner bottom surface of the dish.

SUMMARY OF THE INVENTION

In order to achieve the above described object, a dispensing apparatus according to an aspect of the present invention, includes: a dish mounting portion having a mounting surface configured to be mounted with a dish having a bottom surface and a side surface surrounding the bottom surface; a syringe, arranged above the dish mounting portion, having a nozzle configured to discharge liquid toward an interior of the dish; and a first driving portion configured to rotate an inner bottom surface of the dish mounted on the dish mounting portion with respect to a first axis as a center of rotation, wherein the first axis is parallel to the mounting surface of the dish mounting portion.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which:

FIG. 11A is a diagram describing areas on which liquid discharged from a nozzle of a syringe is not directly poured in a dish; and FIG. 11B is a diagram describing areas on which liquid discharged from a nozzle of a syringe is not directly poured in a dish.

DETAILED DESCRIPTION OF THE INVENTION

At least the following details will become apparent from descriptions of this specification and of the accompanying drawings.

===Configuration of Dispensing Apparatus===

A configuration of a dispensing apparatus 100 according to an embodiment of the present invention will be described with reference to FIG. 1.

Figure 1:
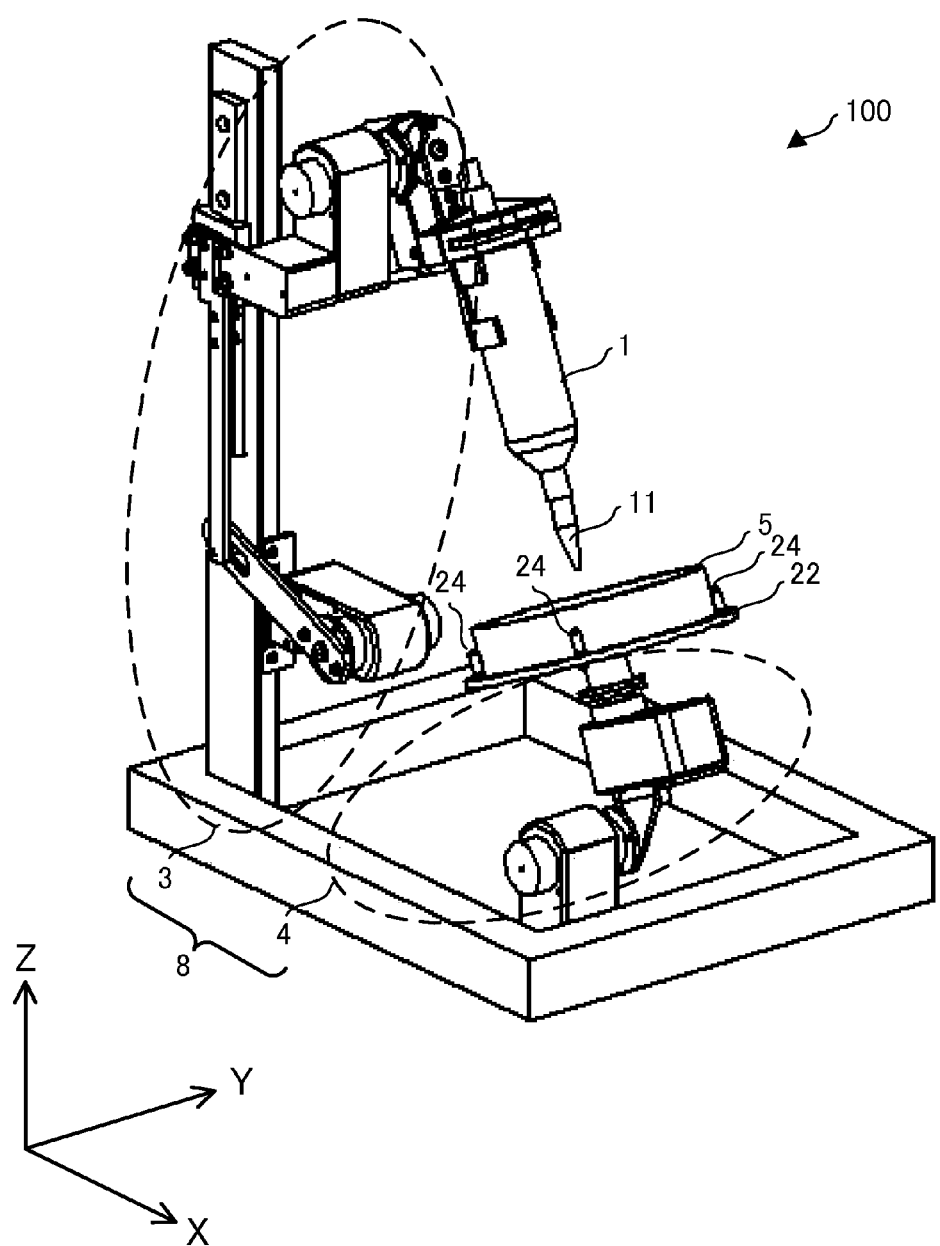
FIG. 1 is an entire configuration diagram of a dispensing apparatus according to an embodiment of the present invention.

FIG. 1 depicts a configuration of cell culture equipment as an example of the application of a dispensing apparatus 100 including a dispensing mechanism 101 according to an embodiment of the present invention. The dispensing apparatus (or cell culture equipment) 100 as illustrated in FIG. 1 is configured including: a syringe 1 for dispensing liquid; and a dish mounting portion 22 which is arranged relatively lower than the syringe 1 and is capable of mounting a dish 5 configured to contain liquid to be dispensed, and further including a driving portion 8 configured to move the syringe 1 and the dish mounting portion 22. The driving portion 8 is configured including a syringe driving portion 3 configured to move the syringe 1 and a dish driving portion 4 configured to move the dish mounting portion 22.

The syringe 1 includes a nozzle 11 configured to discharge liquid.

The dish 5 is a cell culture dish which is formed including a circular bottom surface and a side surface surrounding the circumference of the bottom surface, for example, and is made of resin, for example.

Liquid includes a culture medium for cultivating cells in the dish 5, for example, as well as trypsin and PBS (Phosphate Buffered Saline), for example, depending on purposes.

The dish mounting portion 22 has a flat dish mounting surface 23 in a circular shape to be matched with the circular dish 5, and includes positioning means 24 by which the center of an inner bottom surface of the dish 5 and the center of the dish mounting surface 23 coincide with each other when the dish 5 is mounted and prevented from easily deviating from each other.

The syringe driving portion 3 is capable of controlling the position and the posture of the syringe 1. This enables control of a discharging direction of liquid which is to be discharged from the nozzle 11 of the syringe 1.

The dish driving portion 4 is capable of controlling the position, posture and further rotation of the dish mounting portion 22.

Then, by control of the syringe driving portion 3 and the dish driving portion 4, the relative position between the nozzle 11 of the syringe 1 and the dish 5 is controlled, thereby being able to relatively move the nozzle 11 of the syringe 1 to a position at which liquid is dispensed toward the dish 5.

===Configuration of Dispensing Apparatus===

A configuration of the dispensing mechanism 101 included in the dispensing apparatus 100 according to an embodiment of the present invention will be described with reference to FIG. 2.

Figure 2:
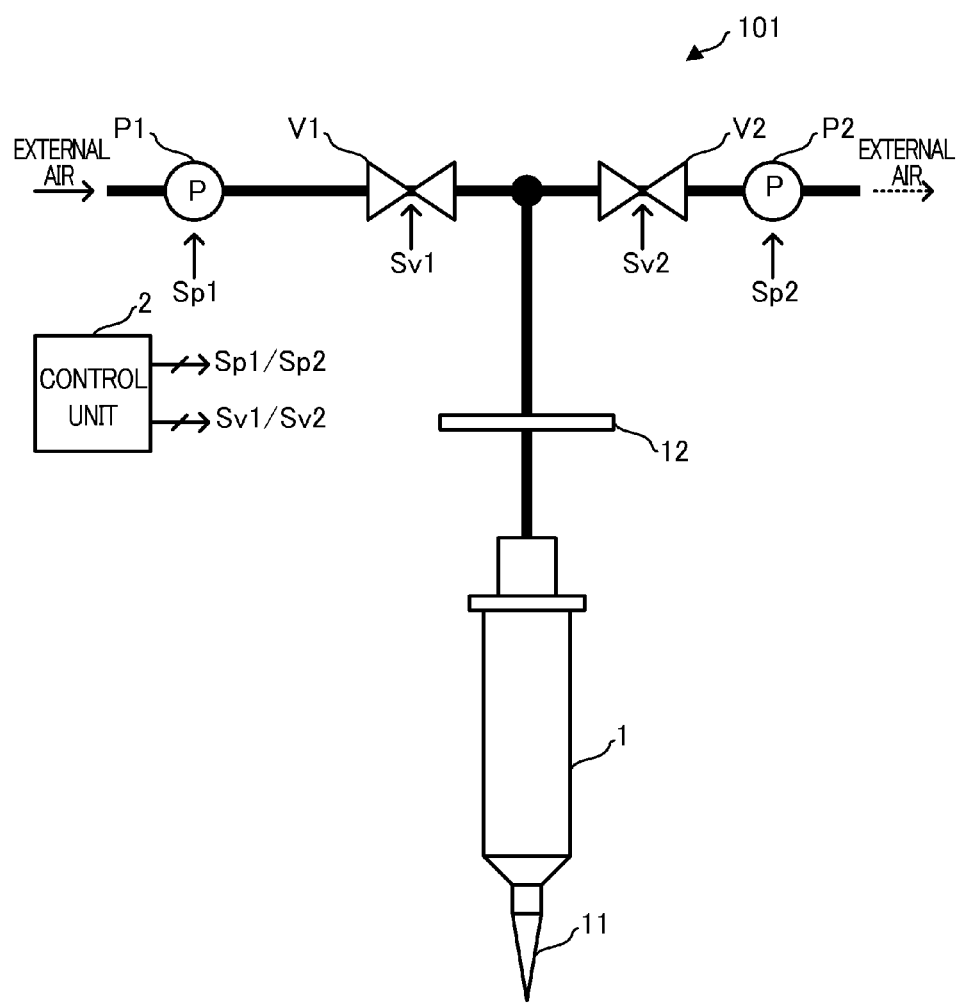
FIG. 2 is a block diagram illustrating a configuration of a dispensing mechanism included in the dispensing apparatus according to an embodiment of the present invention.

The dispensing mechanism 101 as illustrated in FIG. 2 is configured including the syringe 1, a control unit 2, a filter 12, pumps P1 and P2 and valves V1 and V2. The control unit 2 is configured to output control signals Sp1 and Sp2 as well as Sv1 and Sv2 for controlling the pumps and the valves, respectively.

The pump P1 is a pump for discharging configured to introduce the external air into the syringe 1 and generate a pressure to discharge liquid retained in the syringe 1 via the nozzle 11. The pump P2 is a pump for sucking configured to discharge the gas (air) retained in the syringe 1 and generate a pressure (negative pressure) to sucking liquid into the syringe 1 via the nozzle 11.

The valve V1 is connected so as to open/close a passage between the syringe 1 and the pump P1 (i.e., first passage). The valve V2 is connected so as to open/close a passage between the syringe 1 and the pump P2 (i.e., second passage). As each of the valves, a solenoid valve (i.e., electromagnetic valve), a motor-operated pinch valve, etc., for example, that are controllable by a control signal can be used.

The first and the second passages are merged and diverged at one point and the filter 12 such as membrane filter is inserted to a passage between the merging/diverging point and the syringe 1 in order to prevent liquid retained in the syringe 1 from being contaminated by getting mixed with unwanted bacteria. Passages between the external air and the pumps P1 and P2 may also be merged/diverged as appropriate.

===Configuration of Driving Portion===

Subsequently, a configuration of the driving portion 8 will be described with reference to FIG. 3 to FIG. 5.

Figure 3:
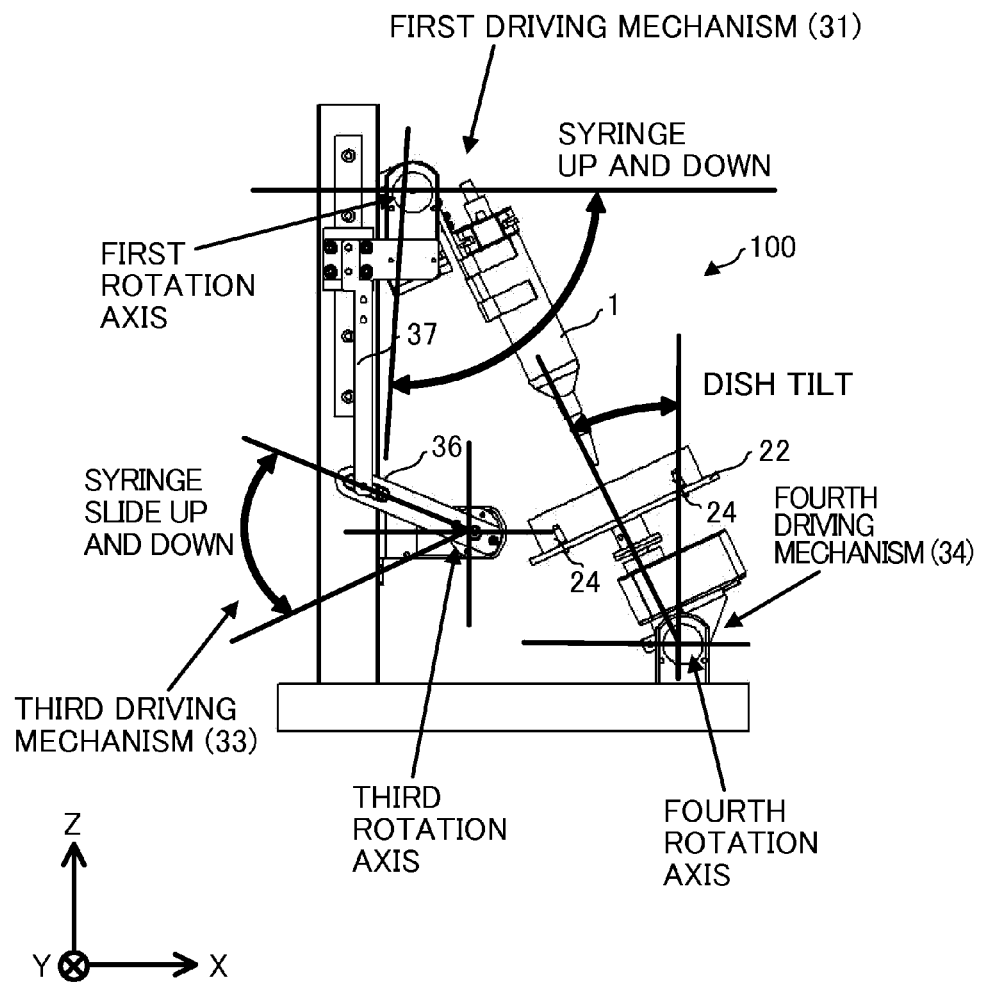
FIG. 3 is a diagram illustrating a first driving mechanism, a third driving mechanism and a fourth driving mechanism according to an embodiment of the present invention.

FIG. 3 is a side view of the dispensing apparatus 100. FIG. 4 is a front view of the dispensing apparatus 100. FIG. 5 is a top surface view of the dispensing apparatus 100.

The syringe driving portion 3 includes a first driving mechanism 31, a second driving mechanism 32 and a third driving mechanism 33. The dish driving portion 4 includes a fourth driving mechanism 34 and a fifth driving mechanism 35.

The first driving mechanism 31 includes a first servo motor 51 in the interior thereof, and as illustrated in FIG. 3, is capable of changing a direction of the nozzle 11 of the syringe 1 with respect to a first rotation axis parallel to a Y axis as the center. The first rotation axis is also orthogonal to a normal (perpendicular line) with respect to the dish mounting surface 23. The direction of the nozzle 11 of the syringe 1 is changed to the direction of a depression angle (first direction) by driving the first servo motor 51. For simplicity of description, the directions in which the nozzle 11 of the syringe 1 is changed by the first servo motor 51 are also referred to as up and down directions.

Figure 4:
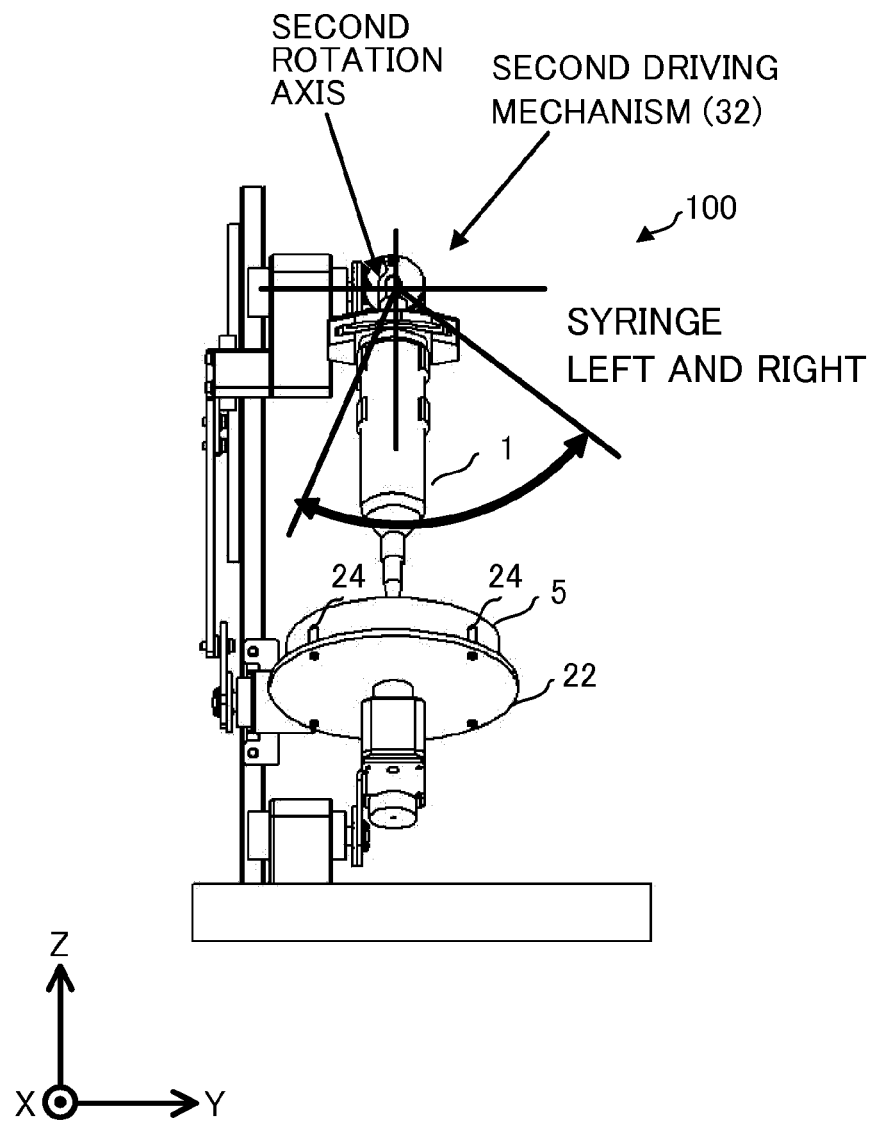
FIG. 4 is a diagram illustrating a second driving mechanism according to an embodiment of the present invention.

The second driving mechanism 32 includes a second servo motor 52 in the interior thereof, and as illustrated in FIG. 4, is capable of changing the direction of the nozzle 11 of the syringe 1 in a plane, which is determined by the direction of the Y axis and the direction of the nozzle 11 of the syringe 1, with respect to a second rotation axis perpendicular to the plane as the center. In an embodiment of the present invention, the second rotation axis is orthogonal to the normal with respect to the dish mounting surface 23 and perpendicular to the first rotation axis, and thus directions of the nozzle 11 to be changed by the second driving mechanism 32 are directions (i.e., second direction) orthogonal to the above described depression angle direction (first direction). For simplicity of description, the directions orthogonal to the depression angle direction are also referred to as left and right directions.

The third driving mechanism 33 includes a third servo motor 53 in an interior thereof, and as illustrated in FIG. 3, is capable of sliding and moving the entire syringe 11 in the direction of the Z axis (vertical direction). The third driving mechanism 33 is configured including a crank structure as illustrated in FIG. 3, wherein an end portion of a first rod 36, configured to be rotationally moved by the third servo motor 53 with respect to a third rotation axis parallel to the Y axis as the center, is connected one end of a second rod 37, and the other end of the second rod is connected to the first driving mechanism 31, the second driving mechanism 32 and the syringe 1. This enables the movement of the syringe 1 in directions toward and away from the dish mounting portion 22.

The fourth driving mechanism 34 includes a fourth servo motor 54 in the internal thereof, and as illustrated in FIG. 3, is capable of changing the inner bottom surface of the dish 5, which is mounted on the dish mounting portion 22, from a horizontal state to a state where it is tilted toward the syringe 1 by rotationally moving the dish mounting portion 22 with respect to a fourth rotation axis (dish first axis) parallel to the Y axis as the center.

Figure 5:
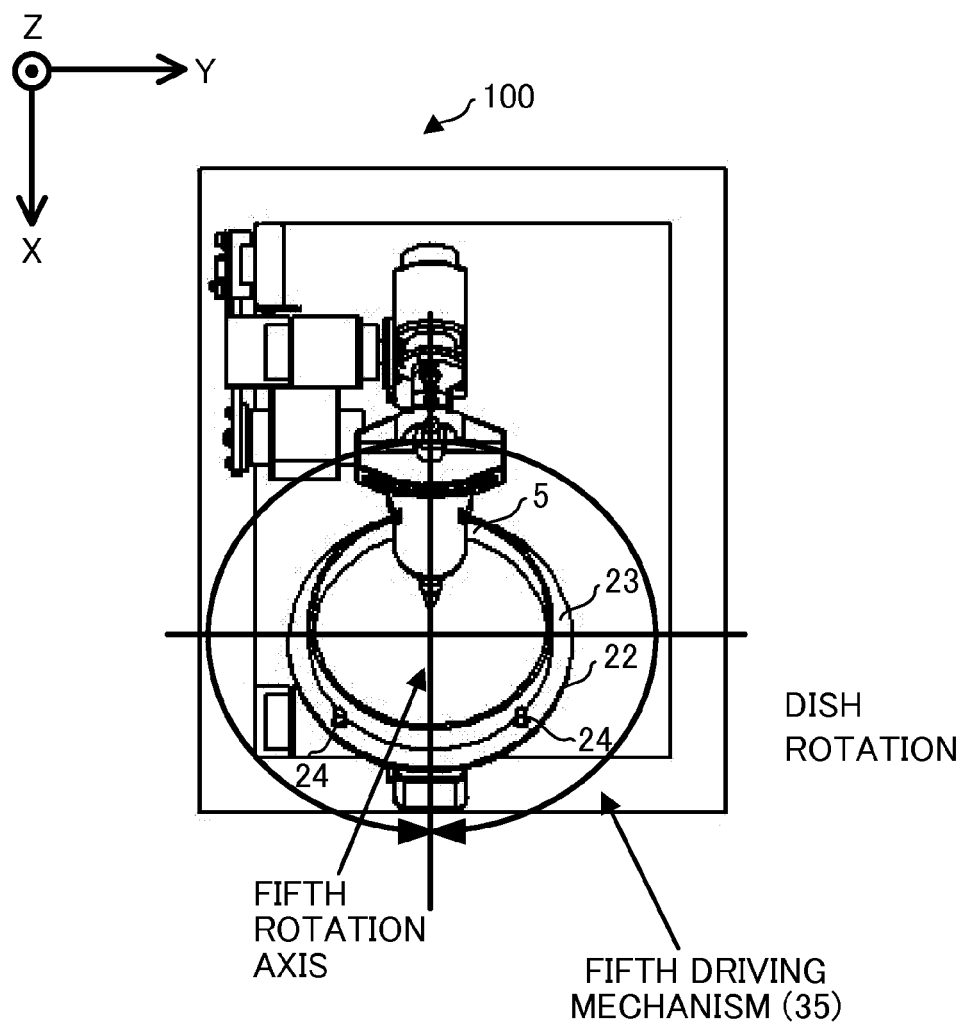
FIG. 5 is a diagram illustrating a fifth driving mechanism according to an embodiment of the present invention.

The fifth driving mechanism 35 includes a fifth servo motor 55 in the interior thereof, and as illustrated in FIG. 5, is capable of rotating the dish mounting portion 22 with respect to a fifth rotation axis (dish second axis) vertical to the dish mounting surface 23 of the dish mounting portion 22 as the center. In an embodiment of the present invention, since the fifth rotation axis runs through the center of the dish mounting surface 23, the dish mounting portion 22 is rotated with respect to the fifth rotation axis as the center, thereby being able to rotate the dish 5 mounted on the dish mounting portion 22 using the center of the bottom surface of the dish 5 as an axis of rotation. The fifth driving mechanism 35 is capable of driving to rotate it in a range of ±180 degrees, for example, using the fifth rotation axis as the center as illustrated in FIG. 5.

The fifth rotation axis of the fifth driving mechanism 35 is arranged so that the fifth rotation axis and the second rotation axis of the second driving mechanism 32 intersect in the same plane. Then, all of the first rotation axis of the first driving mechanism 31, the third rotation axis of the third driving mechanism 33 and the fourth rotation axis of the fourth driving mechanism. 34 are arranged so as to be orthogonal to this plane.

Therefore, the dish mounting portion 22 is tilted toward the syringe 1 by the fourth driving mechanism 34 as well as the direction of the nozzle 11 of the syringe 1 is moved in the up and down directions by the first driving mechanism 31, thereby being able to direct the nozzle 11 of the syringe 1 so as to be perpendicular to the center of the bottom surface of the dish 5 mounted on the dish mounting portion 22.

It is also possible to change the direction of the nozzle 11 of the syringe 1 in the depression angle direction (up and down directions, first direction), that is, the first direction in which two opposing points in areas, in which the inner bottom surface of the dish 5 is in contact with the inner side surface thereof, are connected, by further driving the first driving mechanism 31 based on the direction, in which a normal extends from the nozzle 11 of the syringe 1 to the center of the bottom surface of the dish 5 when the nozzle 11 of the syringe 1 is directed perpendicularly to the center of the bottom surface.

It is also possible to change the direction of the nozzle 11 of the syringe 1 in a direction intersecting with the depression angle direction (left and right directions, second direction) by further driving the second driving mechanism 32 based on the direction in which the normal extends from the nozzle 11 of the syringe 1 to the center of the bottom surface of the dish 5 when the nozzle 11 is directed perpendicularly to the center of the bottom surface.

Then, it is possible to direct the nozzle 11 of the syringe 1 over the entire surface on the inner bottom surface of the dish 5 by combination of the first driving mechanism 31 and the second driving mechanism 32.

For instance, the nozzle 11 of the syringe 1 can be directed to the predetermined position in a ring-shaped area in which the inner bottom surface of the dish 5 is in contact with the inner side surface thereof (e.g., position in the vicinity of the uppermost part of the inner bottom surface of the tilted dish 5 in the ring-shaped area), and the nozzle 11 of the syringe 1 can be further changed in direction so as to be directed along the ring-shaped area.

It is also possible to direct the nozzle 11 of the syringe 1 not only to the ring-shaped area but also to arbitrary positions on the inner bottom surface of the dish 5, and thus the direction of the nozzle 11 of the syringe 1 can be changed along the predetermined route on the inner bottom surface of the dish 5, for example.

It should be noted that each of the first to fifth driving mechanisms 31 to 35 includes a rotary potentiometer, for example, which is capable of detecting a rotational angle of each of the first to fifth rotation axes and position detecting means configured with an origin sensor and a rotary encoder, etc. This enables accurate position control of the syringe 1 and the dish mounting portion 22 performed by the first to fifth driving mechanisms 31 to 35.

Furthermore, an end position of the nozzle at the time of dispensing is set at a position at which the nozzle is not in contact with the bottom surface of the dish 5 as well as dispensed liquid does not splash toward the outside of the dish 5 considering the dispensing flow rate and the moving speed of a nozzle tip.

===Configuration of Control Unit===

Figure 6:
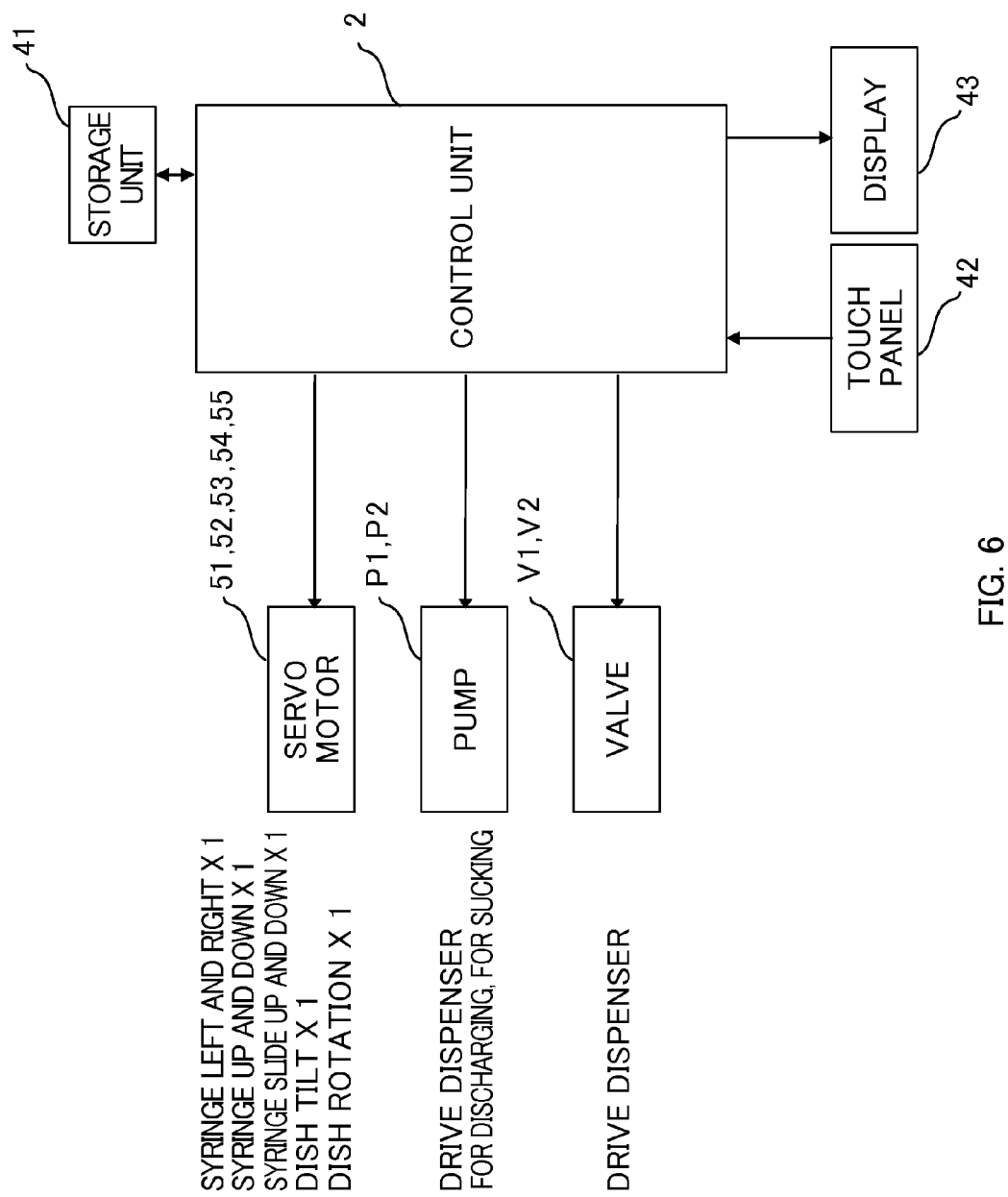
FIG. 6 is a block diagram illustrating a control unit according to an embodiment of the present invention.

As illustrated in FIG. 6, the dispensing apparatus 100 according to an embodiment of the present invention includes the control unit 2, a storage unit 41, the servo motors 51 to 55, the pumps P1 and P2, the valves V1 and V2. The control unit 2 is connected to a touch panel 42 and a display 43.

The touch panel 42 and the display 43 may be realized as constituents of the dispensing apparatus 100 or may also be realized by using an external control device such as personal computer connected to the control unit 2 in a communicable manner.

The control unit 2 is a device configured to control operations of the entire dispensing apparatus 100. The control unit 2 includes a microcomputer capable of executing programs stored in the storage unit 41, for example.

The storage unit 41 is configured to store programs to be executed by the control unit 2 as well as control data and tables to be referred to when the control unit 2 executes the programs.

The touch panel 42 is a device configured to be used by an operator of the dispensing apparatus 100 in order to input various kinds of instructions to the dispensing apparatus 100 such as operation start and operation stop. The operator also inputs, from the touch panel 42, target positions of the syringe 1 and the dish mounting portion 22, positional information of each of the rotation axes of the first to fifth driving mechanisms 31 to 35, or the like, at the initial setting and/or resetting of the dispensing apparatus 100, etc., for example, thereby being able to perform an accurate dispensing operation according to the length of the syringe 1 and the size of the dish 5, etc.

The display 43 is a device configured to output a control state of the dispensing apparatus 100 and various kinds of warnings and the like to the operator of the dispensing apparatus 100.

The control unit 2 is configured to control the servo motors 51 to 55, the pumps P1 and P2 and the valves V1 and V2 by executing programs stored in the storage unit 41 based on the instruction inputted from the touch panel 42.

===Operational Example of Dispensing Apparatus===

Subsequently, an operation of the dispensing apparatus 100 according to an embodiment of the present invention will be described with reference to FIG. 7 to FIG. 10, by giving an example of a series of operations to recover adherent cells, which have been detached by a detachment solution such as trypsin, and floating cells using a medium.

Figure 7:
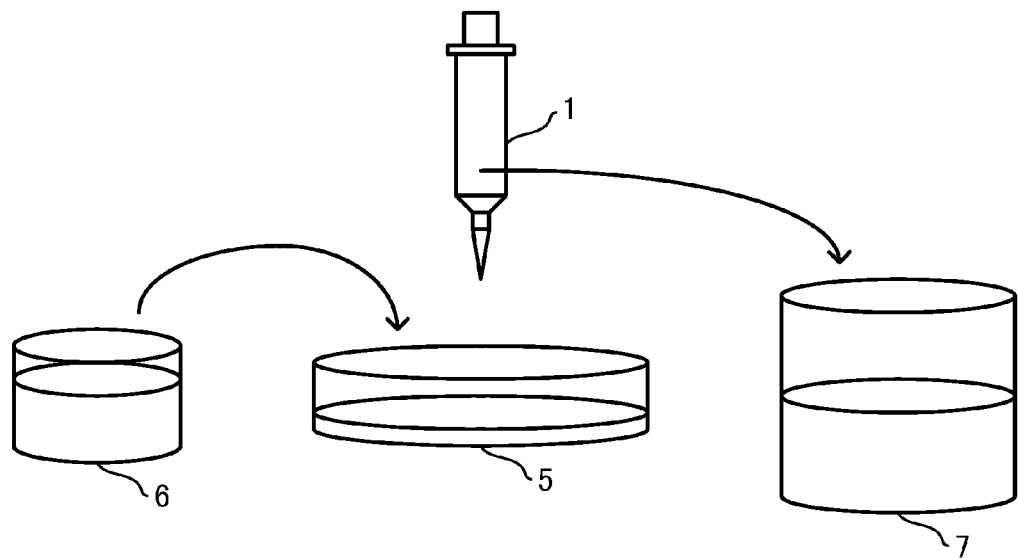
FIG. 7 is a diagram describing an example of operations of filling, dispensing, sucking and discharging liquid using a dispensing apparatus according to an embodiment of the present invention.
Figure 8:
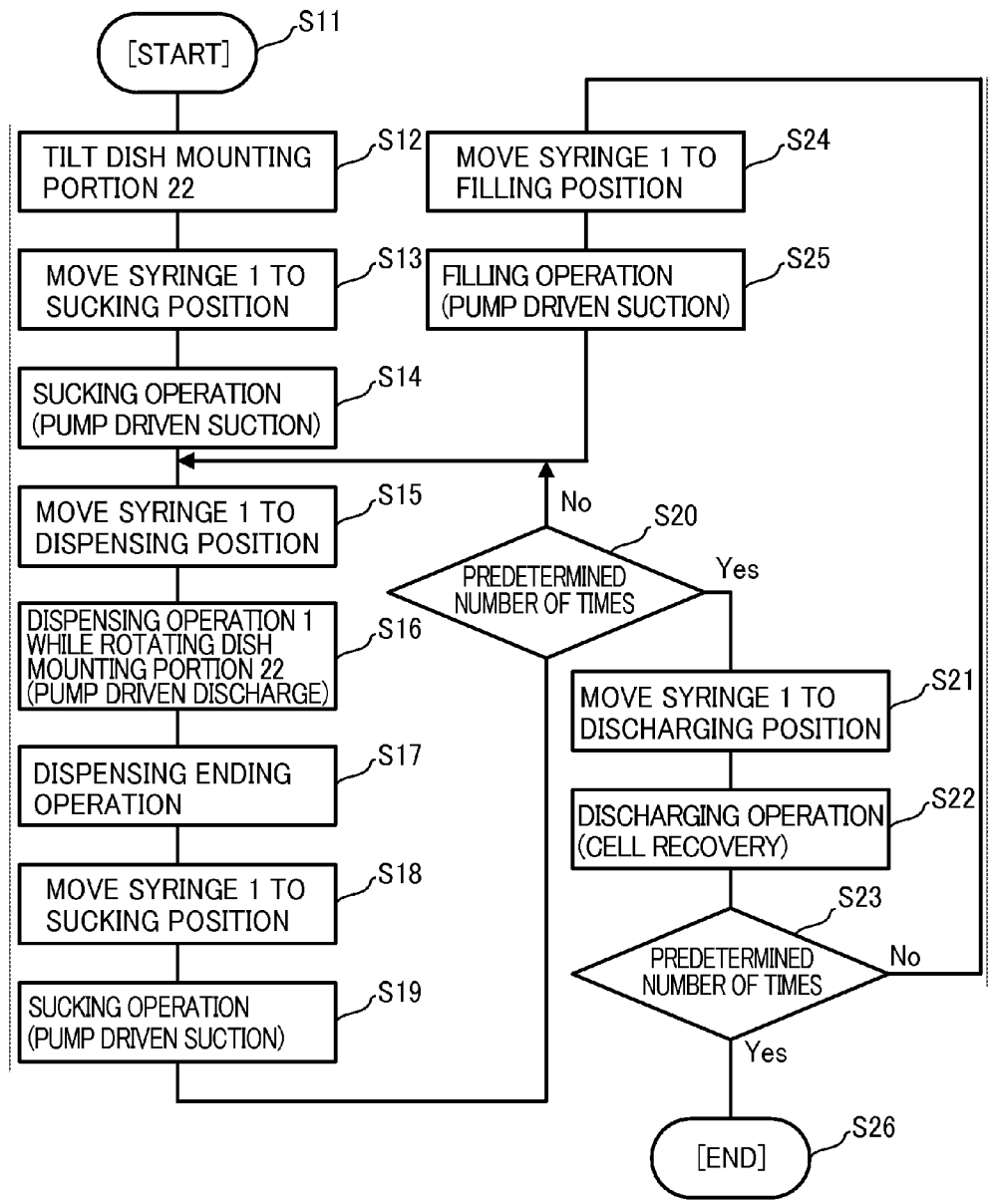
FIG. 8 is a flowchart describing a flow of controlling a dispensing apparatus according to an embodiment of the present invention.

FIG. 7 depicts an outline of an operation to recover cells from the dish 5 using the dispensing apparatus 100 according to an embodiment of the present invention. FIG. 8 exemplifies a flow of controlling the dispensing apparatus 100 when cells are recovered from the dish 5.

In FIG. 7, firstly, the dispensing apparatus 100 sucks liquid, such as medium solution, stored in a reservoir 6 which is provided at a predetermined location in the vicinity of the dispensing apparatus 100, into the syringe 1 (filling operation). The dispensing apparatus 100 then discharges liquid retained in the syringe 1 to the dish 5 (i.e. dispensing operation). The dispensing apparatus 100 then sucks liquid containing cells in the dish 5 into the syringe 1 (i.e. sucking operation) and the liquid retained in the syringe 1 is discharged to a storage tank 7 which is placed at a predetermined location in the vicinity of the dispensing apparatus 100, (i.e. discharging operation). That is, cells are recovered.

Since the filling operation and the sucking operation are the same operation in terms of taking in liquid into the syringe 1, the pumps P1 and P2 and the valves V1 and V2 operate in the same manner. However, the filling operation is an operation to take in liquid from the reservoir 6 into the syringe 1, whereas the sucking operation is different in that liquid is taken in from the dish 5 into the syringe 1, and therefore these operations are described separately for convenience of explanation.

Of course, in addition to the above operations, the dispensing apparatus 100 is also able to suck liquid from the dish 5 so as to discharge the liquid in the reservoir 6, suck liquid from the dish 5 so as to discharge the liquid in the dish 5, and suck liquid from the reservoir 6 so as to discharge the liquid in the reservoir 6. It is also possible to suck liquid from the reservoir 6 so as to discharge the liquid in the storage tank 7.

In the following description, in any case, positions to which the syringe 1 should be moved in order to perform the filling operation, the dispensing operation, the sucking operation and the discharging operation are referred to as a filling position, a dispensing position, a sucking position and a discharging position, respectively.

Next, an example of an operation of recovering a cell which is performed by the dispensing apparatus 100 according to an embodiment of the present invention will be described specifically using a flowchart in FIG. 8. It should be noted that, if the cell to be recovered is an adherent cell, the cell is supposed to have been detached in advance by a detachment solution such as trypsin, and thereafter a medium with serum is poured into the dish 5 to stop a detachment action and the cell results in a state of floating in the medium, being nearly detached and lightly attached, or being deposited on and adhered to the bottom surface of the dish 5. Whereas, if the cell to be recovered is a floating cell, the cell is supposed to be floating in a medium or be deposited on and adhered to the bottom surface of the dish 5.

When the dispensing apparatus 100 starts operating (S11), first, the control unit 2 drives the driving portion 8 to cause the dish mounting portion 22 to be tilted toward the syringe 1 at a predetermined angle (S12). Specifically, the control unit 2 drives the fourth servo motor 54 to cause the dish mounting portion 22 to rotate on the fourth rotation axis (dish first axis). A target rotation amount and a target rotational position are stored in the storage unit 41 in advance. The control unit 2 causes the dish mounting portion 22 to tilt up to a target angle comparing a detection signal from a rotary potentiometer with a target rotation amount and a target rotational position stored in the storage unit 41.

Next, the control unit 2 drives the driving portion 8 to direct the nozzle 11 of the syringe 1 to an sucking position which is a second area (S13), and thereafter performs an operation of sucking liquid retained in the second area containing cells that have been washed off (S14).

The control unit 2 drives the first to third servo motors 51 to 53 in order to direct the syringe 1 to the second area and causes component elements of the first to third driving mechanisms 31 to 33 to rotate at predetermined angles on the first to third rotation axes, respectively. Target rotation amounts or target rotational positions for directing the syringe 1 to the second area are stored in the storage unit 41 in advance. The control unit 2 directs the syringe 1 to the second area while comparing a detection signal from a rotary potentiometer with target rotation amounts and target rotational positions stored in the storage unit 41.

Figure 10A:
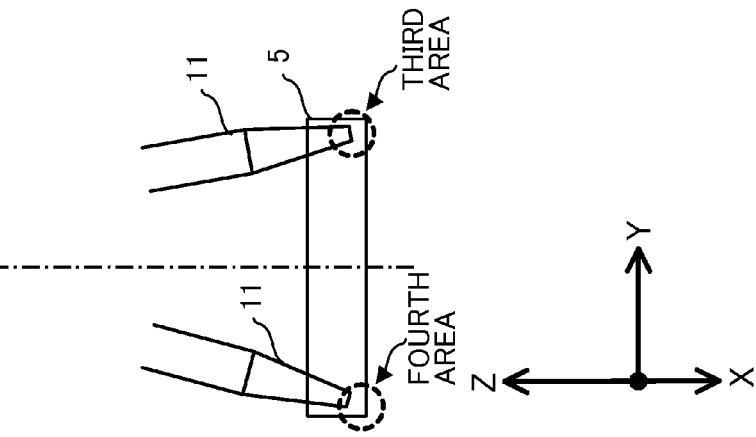
FIG. 10A is a diagram describing control of a dispensing apparatus according to an embodiment of the present invention.

The present dispensing apparatus 100 is capable of changing the direction of the nozzle 11 to the first direction and the second direction based on the direction of a normal which extends from the nozzle 11 of the syringe 1 to the bottom surface of the dish 5 when the nozzle 11 is directed perpendicularly to the bottom surface, thereby being able to direct the nozzle 11 to the second area. Then, as illustrated in FIG. 10A, the nozzle 11 of the syringe 1 can be directed to the second area at predetermined angles with respect to the inner bottom surface and the inner side surface of the dish 5 without interference of the nozzle 11 of the syringe 1 with the bottom surface and the side surface of the dish 5.

As such, the present dispensing apparatus 100 can suck liquid retained in the second area of the tilted dish 5.

Further, the present dispensing apparatus 100 causes the syringe 1 to move in a perpendicularly downward direction by driving the third driving mechanism 33 when the nozzle 11 is directed to the second area. It is therefore possible to arrange the tip of the nozzle 11 in a deepest spot in liquid retained in the second area of the tilted dish 5, thereby being able to recover liquid which has flown down to the second area without leaving the liquid behind therein.

In the sucking operation, under control by the control unit 2, the pump P1 is stopped while the pump P2 is driven to open the valve 2 in a state where the valve V1 is closed, and using pressure (negative pressure) generated in the pump P2, liquid retained in the second area of the dish 5 is sucked from the nozzle 11 of the syringe 1 (pump driven suction).

Next, in the dispensing apparatus 100, the control unit 2 drives the driving portion 8 to direct the nozzle 11 to a dispensing position (S15) based on the direction of a normal extending from the nozzle 11 of the syringe 1 to the bottom surface of the dish 5 when the nozzle 11 is directed perpendicularly to the bottom surface, thereby performing a dispensing operation (S16).

The dispensing position is a predetermined position within a ring-shaped area in which the inner bottom surface of the tilted dish 5 is in contact with the inner side surface thereof, for example.

Figure 9:
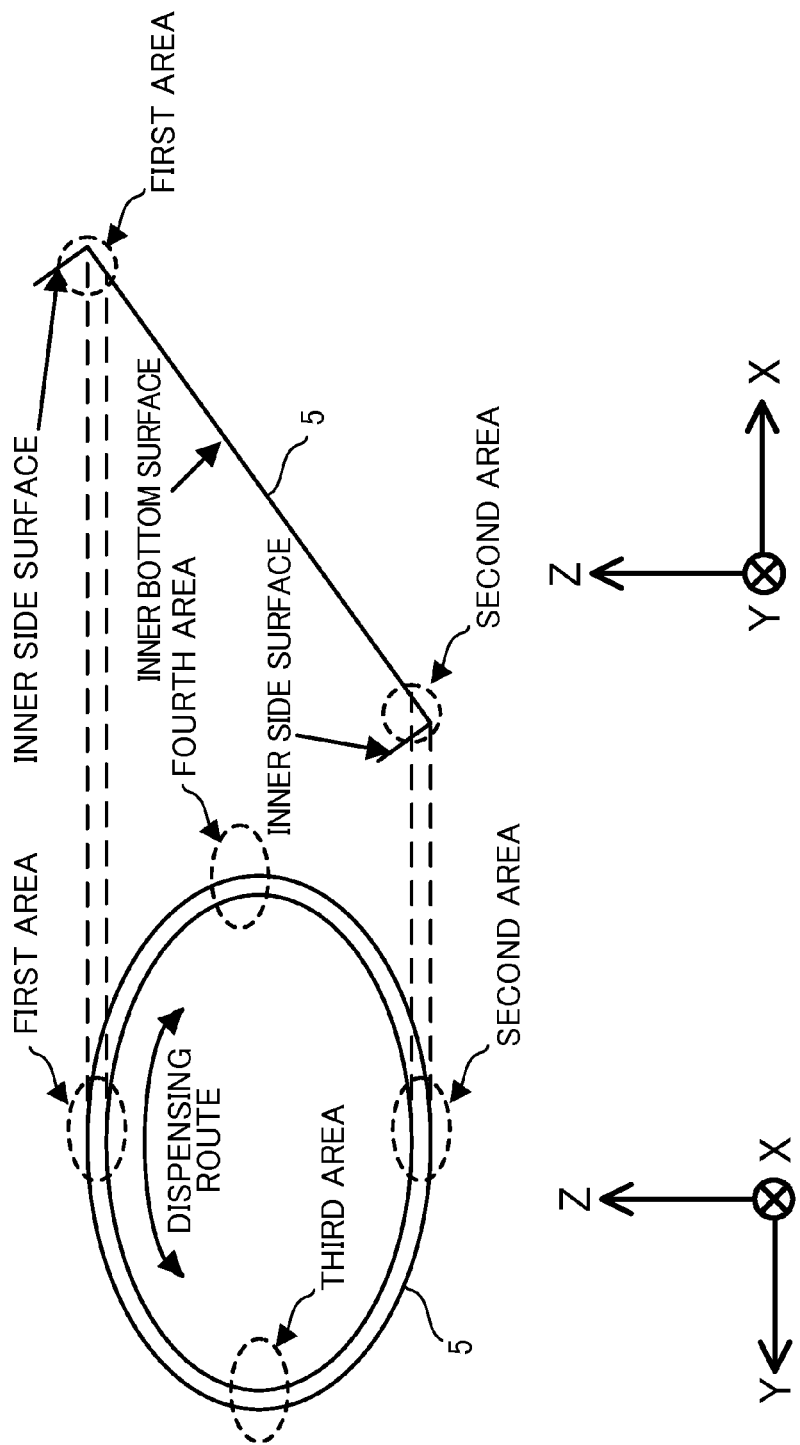
FIG. 9 is a diagram describing control of a dispensing apparatus according to an embodiment of the present invention.

The dispensing position will be described with reference to FIG. 9 and FIG. 10. FIG. 9 is a diagram exemplifying dispensing positions when the dish 5 mounted on the tilted dish mounting portion 22 is viewed from a negative side to a positive side in the X axis direction and viewed from a negative side to a positive side in the Y axis direction.

Figure 10B:
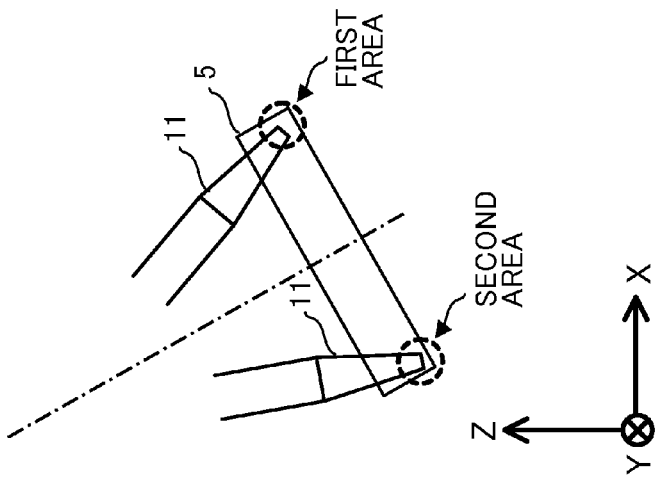
FIG. 10B is a diagram describing control of a dispensing apparatus according to an embodiment of the present invention.

FIG. 10A is a diagram when the dish 5 mounted on the tilted dish mounting portion 22 is viewed from a negative side to a positive side in the Y axis direction, and illustrating respective directions of the nozzle 11 when dispensing positions of the nozzle are in the first area and the second area. FIG. 10B is a diagram when the dish 5 mounted on the tilted dish mounting portion 22 is viewed from a direction parallel to the bottom surface of the dish 5, and illustrating respective directions of the nozzle 11 when dispensing positions of the nozzle are in the first area and the second area.

A dispensing position when performing the dispensing operation in a present embodiment is the first area illustrated in FIG. 9 in the vicinity of the uppermost part in a ring-shaped area in which the inner bottom surface of the tilted dish 5 is in contact with the inner side surface thereof.

The control unit 2 drives the first to third servo motors 51 to 53 to cause component elements of the first to third driving mechanisms 31 to 33 to rotate at predetermined angles on the first to third rotation axes, respectively, in order to direct the syringe 1 to the first area. Target rotation amounts and target rotational positions are stored in the storage unit 41 in advance. The control unit 2 directs the syringe 1 to the first area comparing a detection signal from a rotary potentiometer with target rotations and target rotational positions stored in the storage unit 41.

In the present dispensing apparatus 100, the nozzle 1 can be directed to the first area by changing the direction of the nozzle 11 in the first direction and the second direction based on the direction of a normal extending from the nozzle 11 of the syringe 1 to the bottom surface of the dish 5 when the nozzle 11 is directed perpendicularly to the bottom surface of the dish 5, thereby, as illustrated in FIG. 10A, being able to direct the nozzle 11 of the syringe 1 to the first area at predetermined angles with respect to the inner bottom surface and the inner side surface of the dish 5, without interference of the nozzle 11 with the bottom surface and the side surface of the dish 5.

Return to FIG. 8, in the dispensing operation (S16), under control by the control unit 2, the pump P2 is stopped while the pump P1 is driven to open the valve V1 in a state where the valve V2 is closed, using pressure generated in the pump P1, liquid retained in the syringe 1 is discharged (pump driven discharge).

With respect to the amount of liquid to be discharged from the syringe 1 in the dispensing operation, the relationship between the time to drive the pumps and the amount to be discharged is defined in advance. The storage unit 41 stores data indicative of this relationship, and the control unit 2 controls the valves V1 and V2 and the pumps P1 and P2 so that a predetermined amount of liquid is discharged from the syringe 1.

As such, it becomes possible in the present dispensing apparatus 100 to directly pour liquid discharged with pressure from the nozzle 11 of the syringe 1 toward the above first area of the dish 5. Liquid which has been discharged directly toward the first area flows down while spreading over the inner bottom surface of the dish 5. It is therefore possible to effectively wash away cells that are lightly attached or adhered to the inner bottom surface of the dish 5.

Furthermore, in the dispensing apparatus 100 according to an embodiment of the present invention, when the dispensing operation is executed, the control unit 2 drives the driving portion 8 to cause the dish mounting portion 22 to rotate on a rotation axis passing through the center of the bottom surface of the dish 5 and perpendicular to the bottom surface.

As a result, liquid can be thus discharged while rotating the dish 5, thereby being able to directly pour liquid, discharged with pressure from the nozzle 11 of the syringe 1 to the first area, over the circumference of the inner bottom surface of the dish 5. Thus, it becomes possible to effectively wash off cells that are lightly attached or adhered to the inner bottom surface of the dish 5.

When a predetermined amount of liquid is discharged from the syringe 1, the control unit 2 performs control such that the above described rotation of the dish mounting portion 22 is stopped and discharging of liquid from the syringe 1 is stopped.

The dispensing apparatus 100 performs a dispensing finishing operation (S17). In the dispensing finishing operation, in order to prevent the nozzle 11 of the syringe 1 from dripping droplets and bubbles, for example, the control unit 2 drives the driving portion 8 to bring the tip of the nozzle 11 into contact with the inner side surface of the dish 5, for example, thereby removing droplets and babbles at the tip of the nozzle 11.

When the dispensing finishing operation is ended, a predetermined amount of liquid discharged from the syringe 1 is retained in the second area of the dish 5 as illustrated in FIG. 9. The second area is an area in the vicinity of the lowermost part out of an area in which the inner bottom surface of the dish 5 mounted on the tilted dish mounting portion 22 is in contact with the inner side surface thereof.

Next, the control unit 2 drives the driving portion 8 while discharging of liquid from the syringe 1 is stopped, and directs the nozzle 11 of the syringe 1 to the second area (S18), and thereafter an operation is performed of sucking liquid retained in the second area containing cells that have been washed off (S19).

In order to direct the syringe 1 to the second area, the control unit 2 drives the first to third servo motors 51 to 53 to rotate the component elements of the first to third driving mechanisms 31 to 33 to rotate at predetermined angles on the first to third rotation axes, respectively. Target rotation amounts and target rotational positions for directing the syringe 1 to the second area are stored in the storage unit 41 in advance. The control unit 2 directs the syringe 1 to the second area comparing a detection signal from a rotary potentiometer with target rotation amounts and target rotational positions stored in the storage unit 41.

In the present dispensing apparatus 100, the nozzle 11 of the syringe 1 can be directed to the second area, by changing the direction of the nozzle 11 to the first direction and the second direction based on the direction of a normal extending from the nozzle 11 to the bottom surface of the dish 5 when the nozzle 11 is directed perpendicularly to the bottom surface, thereby, as illustrated in FIG. 10A, being able to direct the nozzle 11 of the syringe 1 to the second area at predetermined angles with respect to the inner bottom surface and the inner side surface of the dish 5, respectively, without interference of the nozzle 11 with the bottom surface and the side surface of the dish 5.

As such, in the present dispensing apparatus 100, liquid retained in the second area of the tilted dish 5 can be sucked.

Further, in the present dispensing apparatus 100, the syringe 1 is moved in a perpendicularly downward direction by driving the third driving mechanism 33 when the nozzle 11 is directed to the second area. Thus, the tip of the nozzle 11 can be arranged in the deepest spot in liquid retained in the second area of the tilted dish 5, thereby being able to recover liquid which has flown down to the second area without leaving the liquid behind therein.

In the sucking operation, under control by the control unit 2, the pump P1 is stopped while the pump 2 is driven to open the valve V2 in a state where the valve V1 is closed, and using pressure (negative pressure) generated in the pump P2, liquid retained in the second area of the dish 5 is sucked from the nozzle 11 of the syringe 1 (pump driven suction).

The dispensing apparatus 100 executes the above described process from S15 to S19 the predetermined number of times, i.e., three to five times in a present embodiment (S20). If the predetermined number of times is set at twice or more, the dispensing apparatus 100 executes the above described process from S15 to S19 until the number of times the process from S15 to S19 is executed reaches the predetermined number of times. By executing the process from S15 to S19 several times, it becomes possible to recover more cells more reliably, when recovering cells lightly attached or adhered to the inner bottom surface of the dish 5.

In the dispensing apparatus 100, when the process from S15 to S19 is executed the predetermined number of times (S20; Yes), the control unit 2 drives the driving portion 8 to move the syringe 1 to an discharging position (S21) in order to perform a discharging operation in which liquid sucked the last time is dispensed in the storage tank 7 (S22). That is, sucked cells are recovered in the tank.

The discharging position is a position at which liquid is discharged from the nozzle 11 provided in a predetermined location.

The control unit 2 drives the first to third servo motors 51 to 53 to rotate the components elements of the first to third driving mechanism 31 to 33 at predetermined angles on the first to third rotation axes, respectively, in order to move the syringe 1 to the discharging position. Target rotation amounts and target rotational positions for moving the syringe 1 to the discharging position are stored in the storage unit 41 in advance. The control unit 2 causes the syringe 1 to move to the discharging position comparing a detection signal from a rotary potentiometer to target rotation amounts and target rotational positions stored in the storage unit 41.

In the discharging operation, similarly to the dispensing operation, under control by the control unit 2, a pump driven discharge is performed, and using pressure generated in the pump P1, liquid, which has been sucked from the second area of the dish 5 into the syringe 1 and contains cells, is discharged into the storage tank 7 (pump driven discharge).

In the discharging operation, it is desirable to take some measures to prevent the surrounding from being contaminated by the pump driven discharge, such as emitting liquid while deeply inserting the nozzle 11 into the storage tank 7 having enough depth, and bringing the tip of the nozzle 11 into contact with the inner wall of the storage tank 7.

The control unit 2 then determines if the discharging operations of S21 and S22, i.e., the recovering process, are executed the predetermined number of times or twice to three times in a present embodiment (S23), and when it reaches the predetermined number of times, a series of the sequences is ended (S26).

On the other hand, when it does not reach the predetermined number of times (S23; No), the control unit 2 drives the driving portion 8 to move the syringe 1 to a filling position (position at which the nozzle 11 of the syringe 1 is in liquid stored in the reservoir 6 in FIG. 7) (S24) and a filling operation is performed (S25).

In the filling operation, under control by the control unit 2, the pump P1 is stopped while the pump P2 is driven to open the valve V2 in a state where the valve V1 is closed, and using pressure (negative pressure) generated in the pump P2, new liquid (e.g., medium) is sucked into the syringe 1 (pump driven suction). When a predetermined amount has been sucked, the pump P2 is stopped to close the valve V2.

Then, returning to the step S15, the control unit 2 executes the process from S15 to S19 the predetermined number of times again. In this case, pouring (dispensing) and sucking are repeated using, e.g., a medium, which is fresh and newly filled from the reservoir 6. As such, in addition to pouring and sucking using the original medium, pouring and sucking using the new medium are further executed, thereby being able to recover cells more reliably. In an embodiment of the present invention, the process is repeated the number of times obtained by (the predetermined number of times of S20)×(the predetermined number of times of S23).

As described above, according to the dispensing apparatus 100 in an embodiment of the present invention, it becomes possible to directly pour liquid discharged from the nozzle 11 of the syringe 1 to any areas including peripheral portions in the inner bottom surface of the dish 5.

Therefore, for example, in the process of recovering cells from the dish 5, more cells that are lightly attached or adhered to the bottom of the dish 5 can be washed away, thereby being able to improve cell recovery efficiency. Further, a sufficient amount of liquid to wash off cells can be directly poured, for a predetermined period of time with a predetermined flow rate, onto such cells that are difficult to be recovered only by flow of liquid flowing down and dispensation of liquid for a short period of time, such as cells that are nearly detached by detachment solution such as trypsin and cells that are deposited on and adhered to the bottom surface of the dish, thereby improving the recovery rate.

As an example, a case of a general-sized dish is considered which is usually called a 100-mm dish. An inner bottom portion of the 100-mm dish is about 90 [mm] in diameter.

When areas on which discharged liquid could not be directly poured by the conventional devices are estimated to be a ring-shaped area of about 5 [mm] in the circumference of the inner bottom portion, an area on which discharged liquid could directly poured by the conventional devices was considered to be only an area of 40 [mm]×40 [mm]× 3.14=5024.0 [mm2].

In the present dispensing apparatus 100, discharged liquid can be poured directly over the entire inner bottom surface, and therefore discharged liquid can be directly poured on an area of 45 [mm]×45 [mm]×3.14=6358.5 [mm2].

When comparing between the above areas, 6358.5 [mm2]/5024.0 [mm2]=1.27 is obtained, and thus efficiency improvement of about 27[%] can be realized.

In the dispensing apparatus 100 according to an embodiment of the present invention, as illustrated in FIG. 9 and FIG. 10, when liquid is discharged from the nozzle 11 of the syringe 1, the nozzle 11 of the syringe 1 is directed to an area (first area) in the vicinity of the uppermost part in a ring-shaped area in which the inner bottom surface of the tilted dish 5 is in contact with the inner side surface thereof. Thus, liquid, which has been directly discharged from the nozzle 11 of the syringe 1 to the above first area, flows down, while spreading over the inner bottom surface of the dish 5, thereby being able to efficiently recover cells that are lightly attached or adhered to the inner bottom surface of the dish 5.

Further, it is also possible to rotate the dish mounting portion 22 on a rotation axis passing through the center of the bottom surface of the dish 5 and perpendicular to the bottom surface when liquid is discharged from the nozzle 11 of the syringe 1. That is, the dish mounting portion 22 is rotated along a plane parallel to the bottom surface of the dish 5. This enables discharging of liquid while rotating the dish 5, thereby being able to directly pour liquid, which has been discharged from the nozzle 11 of the syringe 1 to the above first area, over the circumference of the inner bottom surface of the dish 5. Further, in this case, due to a synergistic effect of the flow of liquid discharged from the nozzle 11 and the rotational speed of the dish 5, the flow velocity of liquid is increased on the inner bottom surface of the dish 5, thereby being able to more efficiently recover cells that are lightly attached or adhered to the dish 5.

When the dish mounting portion 22 is rotated, the dish mounting portion 22 may make one or more rotations in the same direction, for example. This enables directly pouring liquid throughout the entire circumference of the above ring-shaped area of the dish 5.

Alternatively, when the dish mounting portion 22 is rotated, the dish mounting portion 22 may be rotated in the same direction and a reverse direction in an alternate manner. For example, the dish mounting portion 22 may be rotated in the reverse direction every other rotation or may be rotated in the reverse direction every other half rotation. This also enables directly pouring of liquid throughout the entire circumference of the above ring-shaped area of the dish 5. Moreover, particularly, by changing the direction of rotation, liquid discharged from the nozzle 11 can be poured down from a different direction depending on a rotational direction when the liquid is poured down on the dish 5, thereby being able to further improve an effect of recovering cells that are lightly attached or adhered to the dish.

Further, when liquid is discharged from the nozzle 11 of the syringe 1, the direction of the nozzle 11 may be moved from the area in the vicinity of the uppermost part (first area) to the area in the vicinity of the lowermost part (second area) in the ring-shaped area in which the inner bottom surface of the tilted dish 5 is in contact with the inner side surface thereof. This causes liquid which has been discharged from the nozzle 11 of the syringe 1 directly to the above first area to flow down while spreading over the inner bottom surface of the dish 5, as well as the nozzle 11 is moved toward the second area, thereby being able to directly pour liquid to an area on the moving route. Furthermore, in this case, the direction of the nozzle 11 may be combined with a direction in which two areas (third area and fourth area) are connected that oppose to each other in the parallel direction in the ring-shaped area where the inner bottom surface of the tilted dish 5 is in contact with the inner side surface thereof.

Further, when liquid is discharged from the nozzle 11 of the syringe 1, the direction of the nozzle 11 may be moved to up and down directions while being changed alternately to left and right directions (second direction) so as to scan the entire inner bottom surface of the dish 5. This can cause liquid discharged from the nozzle 11 of the syringe 1 to flow down while spreading over the inner bottom surface of the dish 5, as well as cause liquid to be directly poured to a wide area on the route to move the nozzle 11. In this case, the direction of the nozzle 11 may be moved after the dish mounting portion 22 has been fixed. This makes it possible to omit the fifth driving mechanism 35, for example, since rotation of the dish mounting portion 22 is not required.

Furthermore, when performing the dispensing operation, for example, the nozzle 11 of the syringe 1 may be initially directed to the second area illustrated in FIG. 9 (area in the vicinity of the lowermost part in the ring-shaped area in which the inner bottom surface of the tilted dish 5 is in contact with the inner side surface thereof), and then is direct around along the ring-shaped area in which the inner bottom surface of the dish 5 is in contact with the inner side surface thereof. This makes it possible to omit the fifth driving mechanism 35, for example, since rotation of the dish mounting portion 22 is not required.

The above embodiments of the present invention are simply for facilitating the understanding of the present invention and are not in any way to be construed as limiting the present invention. The present invention may variously be changed or altered without departing from its spirit and encompass equivalents thereof.

What is claimed is:

1. A dispensing apparatus comprising:
   A dish mounting portion having a mounting surface configured to be mounted with a dish having a bottom surface and a side surface surrounding the bottom surface;
   A syringe, arranged above the dish mounting portion, having a nozzle configured to discharge liquid toward an interior of the dish;
   A first driving portion configured to rotate an inner bottom surface of the dish mounted on the dish mounting portion with respect to a first axis as a center of rotation, wherein the first axis is parallel to the mounting surface of the dish mounting portion; and
   a second driving portion configured to rotate the dish mounting portion with respect to a second axis as a center of rotation, wherein the second axis is perpendicular to the first axis.

2. The dispensing apparatus according to claim 1, wherein the syringe is moveable such that the nozzle can be directed to an area in which the inner bottom surface of the dish is in contact with an inner side surface thereof.

3. The dispensing apparatus according to claim 1, wherein the syringe is moveable such that the nozzle can be directed to an area in which the inner bottom surface of the dish is in contact with an inner side surface thereof.

4. The dispensing apparatus according to claim 1, further comprising:
   a second driving portion configured to rotate the syringe with respect to a second axis as a center of rotation, wherein the second axis is parallel to the mounting surface of the dish mounting portion.

5. The dispensing apparatus according to claim 3, further comprising:
   a third driving portion configured to rotate the syringe with respect to a third axis as a center of rotation, wherein the third axis is parallel to the mounting surface of the dish mounting portion.

6. The dispensing apparatus according to claim 1, further comprising:
   a second driving portion configured to rotate the syringe with respect to a second axis as a center of rotation, wherein the second axis is coplanar with a normal to the mounting surface of the dish mounting portion and perpendicular to the first axis.

7. The dispensing apparatus according to claim 5, further comprising:

a fourth driving portion configured to rotate the syringe with respect to a fourth axis as a center of rotation, wherein the fourth axis is coplanar with a normal to the mounting surface of the dish mounting portion and perpendicular to the third axis.

8. The dispensing apparatus according to claim 1, further comprising:
a second driving portion configured to move the syringe in a direction toward and away from the dish mounting portion.

9. The dispensing apparatus according to claim 7, further comprising:
a fifth driving portion configured to move the syringe in a direction toward and away from the dish mounting portion.

* * * * *